United States Patent
Yamamoto

(10) Patent No.: US 7,018,950 B2
(45) Date of Patent: Mar. 28, 2006

(54) PROCESS FOR PRODUCING TITANIUM-CONTAINING SILICON OXIDE CATALYST

(75) Inventor: Jun Yamamoto, Sodegaura (JP)

(73) Assignee: Sumitomo Chemical Company, Limited, Osaka (JP)

( * ) Notice: Subject to any disclaimer, the term of this patent is extended or adjusted under 35 U.S.C. 154(b) by 291 days.

(21) Appl. No.: 10/468,366

(22) PCT Filed: Feb. 15, 2002

(86) PCT No.: PCT/JP02/01303

§ 371 (c)(1),
(2), (4) Date: Aug. 19, 2003

(87) PCT Pub. No.: WO02/066157

PCT Pub. Date: Aug. 29, 2002

(65) Prior Publication Data

US 2004/0077886 A1 Apr. 22, 2004

(30) Foreign Application Priority Data

Feb. 22, 2001 (JP) ........................ 2001-046381

(51) Int. Cl.
*B01J 23/00* (2006.01)

(52) U.S. Cl. ...................................... 502/242
(58) Field of Classification Search ................ 502/242
See application file for complete search history.

(56) References Cited

U.S. PATENT DOCUMENTS

| | | | |
|---|---|---|---|
| 4,367,342 A | 1/1983 | Wulff et al. | |
| 4,642,226 A | 2/1987 | Calvert et al. | |
| 6,096,910 A | 8/2000 | Yamamoto et al. | |
| 6,211,388 B1 | 4/2001 | Tsuji et al. | |
| 6,323,147 B1 | 11/2001 | Yamamoto et al. | |
| 6,512,128 B1 | 1/2003 | Yamamoto et al. | |
| 6,551,546 B1 | 4/2003 | Grosch et al. | |
| 2003/0083189 A1 | 5/2003 | Yamamoto et al. | |

FOREIGN PATENT DOCUMENTS

| | | |
|---|---|---|
| EP | 0 077 522 A2 | 4/1983 |
| EP | 0 655 278 A1 | 5/1995 |
| EP | 1 252 928 A1 | 10/2002 |
| EP | 1 364 705 A1 | 11/2003 |
| JP | 8-253314 A | 10/1996 |
| JP | 08-253314 A | 10/1996 |
| JP | 10-017319 A | 1/1998 |
| JP | 2000-107604 A | 4/2000 |
| WO | WO 98/43735 A1 | 10/1998 |
| WO | WO 99/52626 A1 | 10/1999 |
| WO | WO 01/56693 A1 | 8/2001 |

*Primary Examiner*—Bernard Dentz
(74) *Attorney, Agent, or Firm*—Sughrue Mion, PLLC

(57) ABSTRACT

A process for producing a specific titanium-containing silicon oxide catalyst having a specific average pore diameter, a specific a pore diameter distribution and a specific pore volume per unit weight, which comprises the following first to second steps:

first step: a step of obtaining a solid containing a catalyst component and a template by mixing and stirring a silica source, a titanium source and, as the template, the quaternary ammonium ion, wherein an amount of an alkali metal in the mixture prepared is within a range of the following expression (II) or (III), $$\text{alkali metal/titanium} \leq 3 (\text{mol/mol}) \quad \text{(II)}$$

$$\text{alkali metal/}[NR^1R^2R^3R^4]^+ \leq 0.3 (\text{mol/mol}) \quad \text{(III); and}$$

second step: a step of removing the template from the solid prepared in the first step.

1 Claim, No Drawings

PROCESS FOR PRODUCING TITANIUM-CONTAINING SILICON OXIDE CATALYST

TECHNICAL FIELD

The present invention relates to a process for producing a titanium-containing silicon oxide catalyst and said catalyst. More particularly, the present invention relates to a process for producing a titanium-containing silicon oxide catalyst which can be used for reaction of a hydroperoxide with an olefin type compound for obtaining an oxirane compound, and which can exhibit high activity.

BACKGROUND ART

Methods of obtaining an oxirane compound from an olefin type compound and a hydroperoxide in the presence of a catalyst, are publicly known. As a catalyst used herein, for example, U.S. Pat. No. 4,367,342 discloses a specified titanium-supported silicon oxide catalyst. However, it was difficult to say that the conventional catalyst is sufficiently satisfied from the viewpoint of realization of higher activity.

DISCLOSURE OF THE INVENTION

Under the present condition, the problem to be solved by the present invention is to provide, for example, a process for producing a titanium-containing silicon oxide catalyst which can be used for obtaining an oxirane compound from, for example, a hydroperoxide and an olefin type compound, and can exhibit high activity.

Namely, the present invention relates to a process for producing a titanium-containing silicon oxide catalyst satisfying all of the following conditions (1) to (4), which comprises the following first and second steps:

(1): an average pore diameter of 10 Å or more, (2): a pore diameter of 90% or more of the total pore volume of 5 to 200 Å, (3): a specific pore volume of 0.2 cm³/g or more, and (4): a quaternary ammonium ion represented by the following general formula (I) is used as a template and then the template is removed $$[NR^1R^2R^3R^4]^+ \quad (I)$$

(wherein, $R^1$ represents a linear or branched hydrocarbon group having 2 to 36 carbon atoms, and $R^2$ to $R^4$ represent an alkyl group having 1 to 6 carbon atoms)

first step: a step of obtaining a solid containing a catalyst component and a template by mixing and stirring a silica source, a titanium source and, as the template, the quaternary ammonium ion, wherein an amount of an alkali metal in the mixture prepared is within a range of the following expression (II) or (III), $$\text{alkali metal/titanium} \leq 3 (\text{mol/mol}) \quad (II)$$

$$\text{alkali metal/}[NR^1R^2R^3R^4]^+ \leq 0.3 (\text{mol/mol}) \quad (III); \text{ and}$$

second step: a step of removing the template from the solid prepared in the first step.

BEST MODE FOR CARRYING OUT THE INVENTION

The catalyst obtained by the present invention is a titanium-containing silicon oxide catalyst satisfying all of the following conditions (1) to (4).

The condition (1) is that an average pore diameter of the catalyst is 10 Å or more.

The condition (2) is that a pore diameter of 90% or more of the total pore volume of the catalyst is 5 to 200 Å.

The condition (3) is that a specific pore volume of the catalyst is 0.2 cm³/g or more. Herein, the specific pore volume means pore volume per 1 g of the catalyst.

Measurements of these conditions (1) to (3) can be conducted by ordinary methods such as a physical absorption method using gas such as nitrogen, argon or the like.

The condition (4) is that the catalyst is obtained by using a quaternary ammonium ion represented by the following general formula (I) as the template and then removing the template;

$$[NR^1R^2R^3R^4]^+ \quad (I)$$

(wherein, $R^1$ represents a linear or branched hydrocarbon group having 2 to 36 carbon atoms, and $R^2$ to $R^4$ represent an alkyl group having 1 to 6 carbon atoms).

The condition (4) will be illustrated in detail in a part of a process for producing said catalyst.

The catalyst of the present invention may or may not have a peak showing an interplanar spacing (d) in a X-ray diffraction (XRD). The peak showing an interplanar spacing (d) as herein referred to means a peak derived from the crystallinity and regularity of a solid, and abroad peak derived from an amorphous part may exist.

The catalyst obtained in the present invention preferably has an absorption peak in the region of 960±5 cm⁻¹ in the infrared absorption spectrum from the viewpoint of high activity. This peak is assumed to correspond to that of titanium introduced into the silica skeleton.

The first step of the production process of the present invention is a step of obtaining a solid containing a catalyst component and a template by mixing and stirring a silica source, a titanium source, and, as the template, a quaternary ammonium ion, wherein an amount of an alkali metal in the mixture prepared is within a range of the following expression (II) or (III).

$$\text{alkali metal/titanium} \leq 3 (\text{mol/mol}) \quad (II)$$

$$\text{alkali metal/}[NR^1R^2R^3R^4]^+ \leq 0.3 (\text{mol/mol}) \quad (III)$$

When the reagent to be used in the first step is solid, it is preferable to be used as a solution by dissolving or dispersing it in a solvent.

The silica source includes amorphous silica and alkoxysilane such as tetramethyl orthosilicate, tetraethyl orthosilicate, tetrapropyl orthosilicate and the like.

The titanium source includes titanium alkoxides such as tetramethyl titanate, tetraethyl titanate, tetrapropyl titanate, tetraisopropyl titanate, tetrabutyl titanate, tetraisobutyl titanate, tetra-2-ethylhexyl titanate, tetraoctadecyl titanate; and titanium (IV) oxyacetylacetonate, titanium (IV) diisopropoxybisacetylacetonate and the like; and titanium halides such as titanium tetrachloride, titanium tetrabromide and titanium tetraiodide, titanyl sulfate and the like.

As the template, a quaternary ammonium ion represented by the general formula (I) is used.

$$[NR^1R^2R^3R^4]^+ \quad (I)$$

(wherein, $R^1$ represents a linear or branched hydrocarbon group having 2 to 36 carbon atoms, and $R^2$ to $R^4$ represent an alkyl group having 1 to 6 carbon atoms).

$R^1$ is a linear or branched hydrocarbon group having 2 to 36 carbon atoms, preferably 10 to 18 carbon atoms.

$R^2$ to $R^4$ are an alkyl group having 1 to 6 carbon atoms, and preferably each of $R^2$ to $R^4$ is a methyl group.

Specific examples of the quaternary ammonium ion represented by the general formula (I) include cations such as hexadecyltrimethylammonium, dodecyltrimethylammonium, benzyltrimethylammonium, dimethyldidodecylammonium, hexadecylpyridinium, and the like.

Further, these quaternary ammonium ions represented by the general formula (I) may be used alone or may be used as a mixture of two or more kinds.

Examples of the solvent include water and alcohols such as methanol, ethanol, n-propanol, 2-propanol, n-butanol, sec-butanol, t-butanol, allyl alcohol, cyclohexanol, benzyl alcohol and the like, and diols, mixtures thereof and the like.

The amount used of the titanium source based on the silica source is preferably from $10^{-5}$ to 1, more preferably from 0.00008 to 0.4 in terms of molar ratio. The amount used of the quaternary ammonium ion based on the total amounts of silica source and titanium source is preferably from $10^{-2}$ to 2 in terms of molar ratio.

Further, for promoting the reaction of the silica source with the titanium source, it is preferable to impart alkalinity or acidity to the mixed solution. As the alkali source, quaternary ammonium hydroxides are preferable, and examples thereof include tetramethylammonium hydroxide, tetraethylammonium hydroxide, tetrapropylammonium hydroxide and the like, and a hydroxide of the quaternary ammonium ion represented by the general formula (I) is more preferably used. Examples of the acid include inorganic acids such as hydrochloric acid, sulfuric acid, nitric acid and the like, and organic acids such as formic acid, acetic acid, propionic acid and the like.

The mixing and stirring temperature is usually from −30 to 100° C. Solid is formed by mixing and stirring, and the solid may be aged for further growth thereof. The aging time is usually 180 hours or less, and the aging temperature is usually from 0 to 200° C. When heating is required in aging, it is preferable that the mixture is transferred into a pressure vessel and heating is conducted in a closed pressure vessel for avoiding vaporization of the solvent.

To attain the object of the present invention, which is to obtain a catalyst having an extremely high activity, it is necessary that the amount of the alkali metal in the mixture prepared is within a range of the following expression (II) or (III):

$$\text{alkali metal/titanium} \leq 3 (\text{mol/mol}) \quad \text{(II)}$$

$$\text{alkali metal/}[NR^1R^2R^3R^4]^+ \leq 0.3 (\text{mol/mol}) \quad \text{(III)},$$

further preferably $$\text{alkali metal/titanium} \leq 1 (\text{mol/mol}) \quad \text{(II)}$$

$$\text{alkali metal/}[NR^1R^2R^3R^4]^+ 0.1 (\text{mol/mol}) \quad \text{(III)}.$$

When the amount of the alkali metal in the mixture prepared is beyond the ranges of the expression (II) and (III), it is difficult to obtain a catalyst having an extremely high activity.

Examples of the alkali metal include lithium, sodium, potassium, rubidium, cesium and the like, and the alkali metal usually exists in an ionic state.

The solid obtained in the first step is usually filtered and dried. The temperature during drying is 120° C. or lower, preferably 100° C. or lower. The atmosphere for drying includes air or inert gas such as nitrogen or the like. As a drying apparatus, a conical dryer or plate dryer, equipped with a warm current device or vacuum device can be listed. Besides, in vacuum drying, it is preferable to dry under a vacuum of 200 mmHg or lower from the viewpoint of improving of drying efficiency at low temperature.

The second step of the present invention is a step of removing the template from the solid. The removal of the template can be easily accomplished by calcining the solid containing the catalyst component and the template obtained in the first step under air at a high temperature of 400 to 700° C., or by subjecting to solvent extraction, and among these, it is preferable to remove the template by a solvent extraction. A technique for extracting a template with a solvent is reported by Whitehurst et al. (see U.S. Pat. No. 5,143,879)

The solvent used in extraction may include a solvent which can dissolve a compound used as the template, and oxa- and/or oxo-substituted hydrocarbons having carbon atoms of 1 to about 12 in a liquid state at room temperature can be generally used. Suitable examples of such solvents include alcohols, ketones, (acyclic and cyclic)ethers and esters. Examples thereof include hydroxy-substituted hydrocarbons such as methanol, ethanol, ethylene glycol, propylene glycol, isopropanol, n-butanol or octanol; oxo-substituted hydrocarbons such as acetone, diethyl ketone, methyl ethyl ketone or methyl isobutyl ketone; ethers of a hydrocarbon such as diisobutyl ether and tetrahydrofuran; esters of a hydrocarbon such as methyl acetate, ethyl acetate, butyl acetate or butyl propionate, and the like.

The weight ratio of the solvent to the catalyst is usually from 1 to 1000, preferably from 5 to 300.

For improving efficiency of the extraction, acids or salts thereof may be added to these solvents.

Examples of acids used include inorganic acids such as hydrochloric acid, sulfuric acid, nitric acid, bromic acid and the like, organic acids such as formic acid, acetic acid, propionic acid and the like. Examples of salts thereof include alkali metal salts, alkaline earth metal salts, ammonium salts and the like.

The concentration in the solvent of the acid or salt thereof to be added is preferably 10 mol/l or less, further preferably 5 mol/l or less. When the concentration in the solvent of the acid or salt to be added is too high, the catalytic activity may be lowered by elution of titanium in the catalyst.

After adequately mixing a catalyst with a solvent, the liquid portion is separated by filtration, decantation or the like. This operation is repeated required times. Extraction can be also conducted by a method of flowing a solvent for washing into a catalyst layer. The completion of washing can be known by, for example, analyzing the liquid portion. The extraction temperature is preferably 0 to 200° C., further preferably 20 to 100° C.

Instead of using the above-mentioned solvent, extraction can be also conducted by using a super critical fluid. As the super critical fluid, carbon dioxide is preferable. The critical temperature of carbon dioxide is about 31° C. or more. Therefore, the extraction temperature is preferably 31 to 100° C., further preferably 35 to 60° C. The critical pressure of carbon dioxide is about 7.4 MPa, so the extraction pressure is preferably 10 to 30 MPa. The amount of super critical carbon dioxide used for extraction is preferably 50 to 500 g/min. per 1 liter of catalyst, and the extraction time is preferably 4 to 20 hours.

The solid obtained after the extraction may be dried. Namely, it is preferable to heat at a temperature of 10 to 800° C., further preferably 50 to 300° C. under a reduced pressure or an atmosphere of non-reducing gas such as nitrogen, argon, carbon dioxide or oxygen-containing gas such as air.

The quaternary ammonium ion represented by the general formula(I) in the solution obtained after the extraction, is recovered and can be also recycled as a template material in the first step.

When a hydroxide of a quaternary ammonium ion represented by the general formula (I) is used, a desired raw material is obtained by ion-exchange of the quaternary ammonium salt in the solution obtained after the extraction.

The ion-exchange can be accomplished by mixing the quaternary ammonium salt in the solution with a hydroxide of alkali metal in a solvent such as methanol or the like, or by contacting an ion-exchange resin adjusted with an alkali metal hydroxide, with a solution containing a quaternary ammonium salt. However, as the conditions, it is essential to select conditions so that the amount of the alkali metal ion becomes within the range of the above described formula (II) or (III).

In addition, the solvent used for extraction can be recovered by usual method such as distillation or the like and recycled.

In the production of the catalyst, it is preferable to adopt a step of subjecting the catalyst to silylation from the viewpoint of heightening of the catalyst activity.

The silylation is conducted by contacting the catalyst obtained in the second step with a silylation agent thereby converting a hydroxyl group existing on the surface of the catalyst into a silyl group.

Examples of the silylation agent include organic silanes, organic silylamines, organic silylamides and derivatives thereof, and organic silazanes and other silylation agents.

Examples of the organic silane include chrolotrimethylsilane, dichlorodimethylsilane, chlorobromodimethylsilane, nitrotrimethylsilane, chlorotriethylsilane, iododimethylbutylsilane, chlorodimethylphenylsilane, chlorodimethylsilane, dimethyl-n-propylchlorosilane, dimethylisopropylchlorosilane, t-butyldimethylchlorosilane, tripropylchlorosilane, dimethyloctylchlorosilane, tributylchlorosilane, trihexylchlorosilane, dimetylethylchlorosilane, dimethyloctadecylchlorosilane, n-butyldimethylchlorosilane, bromomethyldimethylchlorosilane, chloromethyldimethylchlorosilane, 3-chloropropyldimethylchlorosilane, dimethoxymethylchlorosilane, methylphenylchlorosilane, triethoxychlorosilane, dimethylphenylchlorosilane, methylphenylvinylchlorosilane, benzyldimethylchlorosilane, diphenylchlorosilane, diphenylmethylchlorosilane, diphenylvinylchlorosilane, tribenzylchlorosilane, 3-cyanopropyldimethylchlorosilane.

Examples of the organic silylamine include N-trimethylsilylimidazole, N-t-butyldimethylsilylimidazole, N-dimethylethylsilylimidazole, N-dimethyl-n-propylsilylimidazole, N-dimethylisopropylsilylimidazole, N-trimethylsilyldimethylamine, N-trimethylsilyldiethylamine, N-trimethylsilylpyrrole, N-trimethylsilylpyrrolidine, N-trimethylsilylpiperidine, 1-cyanoethyl(diethylamino)dimethylsilane, pentafluorophenyldimethylsilylamine.

Examples of the organic silylamide and derivatives include N,O-bistrimethylsilylacetamide, N,O-bistrimethylsilyltrifluoroacetamide, N-trimethylsilylacetamide, N-methyl-N-trimethylsilylacetamide, N-methyl-N-trimethylsilyltrifluoroacetamide, N-methyl-N-trimethylsilylheptafluorobutylamide, N-(t-butyldimethylsilyl)-N-trifluoroacetamide, N,O-bis(diethylhydrosilyl)trifluoroacetamide.

Examples of the organic silazane include hexamethyldisilazane, heptamethyldisilazane, 1,1,3,3-tetramethyldisilazane, 1,3-bis(chloromethyl)tetramethyldisilazane, 1,3-divinyl-1,1,3,3-teteramethyldisilazane, 1,3-diphenyltetramethyldisilazane.

Examples of the other silylation agent include N-methoxy-N,O-bistrimethylsilyltrifluoroacetamide, N-methoxy-N,O-bistrimethylsilyl carbamate, N,O-bistrimethylsilyl sulfamate, trimethylsilyltrifluoromethane sulfonate, N,N'-bistrimethylsilylurea. The preferable silylation agent is hexamethyldisilazane.

The catalyst of the present invention is usually used as a molded catalyst via a step for molding a solid containing the catalyst component. Though the molding step may be conducted in any stage, before or after the above-mentioned template-removing step, or after the silylation step, it is preferable to conduct before the template-removing step from the viewpoint of suppression of degradation of catalyst properties such as specific surface area, pore volume and the like. As the molding method, any method such as compression molding, extrusion molding or the like may be used. An organic or inorganic binder usually used can be used in the extrusion molding, but lowering of catalyst activity may be caused by addition of a binder. In the production of the molded catalyst, the compression molding is the most preferable from the viewpoint of strength and physical properties of the catalyst.

As the compression molding, a roll press molding (briquetting, compacting), oil hydraulic press molding, tabletting and the like can be listed. The pressure in compression is usually 0.1 to 10 ton/cm$^2$, preferably 0.2 to 5 ton/cm$^2$, further preferably 0.5 to 2 ton/cm$^2$. When the pressure is too low, the strength of a molded body is sometimes inadequate. On the other hand, when the pressure is too high, the physical properties of the catalyst sometimes become inadequate because pores are broken. In carrying out the compression molding, it is preferable that a solid containing a catalyst component contains water in a proper amount, and a molded body having a sufficient strength can be produced by this. The water content of the material to be subjected to the compression molding is preferably 1 to 70% by weight, further preferably 5 to 40% by weight. The water amount may be adjusted by a dryness degree during drying of a wet solid, and may be adjusted by adding water to an adequately dried solid.

In addition, a binder usually used and the like may be added within a range of no obstacle to a desired performance.

The shape of the molded body may be any shape such as tablet, sphere, ring or the like. The molded body may be used as it is or after pulverizing to a proper size.

The catalyst of the present invention can be used for selective oxidation, for example, in addition to epoxidation of an olefin type compound, various oxidation reactions of organic compounds because the catalyst has a high specific surface area and highly dispersed titanium active sites. Further, if desired, it is also possible to intensify acid sites of the catalyst with addition of a third component such as alumina, etc., and the catalyst can be used for alkylation, catalytic reforming, etc.

The catalyst of the present invention can be optimally can be used for production of an oxirane compound in which an olefin type compound is reacted with a hydroperoxide, in particular.

The olefin type compound may be acyclic, mono-cyclic, di-cyclic or poly-cyclic compounds, and mono-olefin type, di-olefin type or poly-olefin type compounds. When the number of olefin bonds is two or more, these may be a conjugated bond or non-conjugated bond. Olefin type compounds having 2 to 60 carbon atoms are usually preferred. These may have a substituent, and the substituent is preferably a relatively stable substituent. Examples of such the hydrocarbon include ethylene, propylene, 1-butene, isobutylene, 1-hexene, 2-hexene, 3-hexene, 1-octene, 1-decene, styrene, cyclohexene, and the like. Apt examples of the di-olefin type compound include butadiene and isoprene. A substituent may exist, and as the example thereof, a halogen is listed, further various substituents containing an oxygen, sulfur or nitrogen atom together with a hydrogen and/or carbon atom, may exist. A particularly preferable olefin type compound is an olefin type unsaturated alcohol and an olefin type unsaturated hydrocarbon substituted with a halogen, and as examples thereof, allyl alcohol, crotyl alcohol, allyl chloride are listed. Particularly preferable compound is an alkene having 3 to 40 carbon atoms, and this compound may be substituted with a hydroxy group or halogen atom.

As examples of a hydroperoxide, organic hydroperoxides can be listed.

The organic hydroperoxide is a compound represented by the general formula;

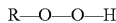

(wherein, R represents a hydrocarbyl group), and is reacted with an olefin type compound to produce an oxirane compound and compound, R—OH. Preferably, the group R is a group having 3 to 20 carbon atoms. Most preferably, this is a hydrocarbyl group having 3 to 10 carbon atoms, particularly a secondary or tertiary alkyl group or aralkyl group. Among them, tertiary alkyl groups, and secondary or tertiary aralkyl groups are particularly preferable, and specific examples thereof include a tertiary butyl group, tertiary pentyl group, cyclopentyl group, and 2-phenylpropyl-2- group. Further, various tetralinyl groups formed by eliminating hydrogen from an aliphatic side chain of a tetralin molecule, are also listed.

When cumene hydroperoxide as the organic hydroperoxide is used, the resulting hydroxyl compound is 2-phenyl-2-propanol. This can be converted to α-methyl styrene by dehydration reaction. α-methyl styrene is a industrially useful substance.

Tertiary amylene formed by dehydration of tertiary pentyl alcohol obtained by using t-pentyl hydroperoxide as the organic hydroperoxide, is a useful substance as a precursor of isoprene. Tertiary pentyl alcohol is useful as a precursor of methyl tertiary pentyl ether which is an octane booster.

Tertiary butyl alcohol obtained by using t-butyl hydroperoxide as an organic hydroperoxide is useful as a precursor of methyl tertiary butyl ether which is an octane booster.

Hydrogen peroxide can be listed as an example other than organic hydroperoxides.

Hydrogen peroxide is a compound represented by the chemical formula, HOOH, and can be obtained usually in the form of an aqueous solution. It reacts with an olefin type compound to form an oxirane compound and water.

The organic hydroperoxide and hydrogen peroxide, which are used as a raw material, may be a thin or dense purified or non-purified material.

The epoxidation can be carried out in a liquid phase by using a solvent and/or a diluent. The solvent and diluent are a substance which are liquid under the pressure and temperature under which the reaction is conducted, and must be substantially inert against the reactants and products. The solvent may be a substance existing in the hydroperoxide solution to be used. For example, when cumene hydroperoxide is a mixture of cumene hydroperoxide and cumene, which is a raw material thereof, said cumene hydroperoxide can be used as a substitute for the solvent without especially adding a solvent.

The epoxidation temperature is usually from 0 to 200° C., preferably from 25 to 200° C. The pressure may be a pressure enough to keep the reaction mixture liquid. Usually, the pressure is advantageously from 100 to 10000 kPa.

After completion of the epoxidation, a liquid mixture containing desired product is easily separated from a catalyst composition. Next, the liquid mixture is purified by a suitable method. Purification includes fractional distillation, selective extraction, filtration, washing and the like. The solvent, catalyst, non-reacted propylene and non-reacted hydroperoxide can be used again by recycling.

The reaction, in which the catalyst of the present invention is used, can be carried out in the form of a slurry or a fixed bed, and, in the case of a large scale of industrial operation, it is preferable to use a catalyst in the form of a fixed bed. The present process can be carried out by a batchwise method, semi-continuous method or continuous method. When a solution containing a reactant is introduced through a fixed bed, a liquid mixture obtained from a reaction zone does not contain catalyst at all or contains substantially no catalyst.

EXAMPLE

The present invention is illustrated by the following Examples.

Example 1

Preparation of Catalyst

While 375.3 g of 16 wt % hexadecyltrimethyl ammonium hydroxide aqueous solution (containing 0.1% by weight of K ion) was stirred, 5.55 g of tetra-isopropyl orthotitanate and 30.0 g of 2-propanol were added dropwise to this. After stirring of 30 minutes, 114.3 g of tetramethyl orthosilicate was added dropwise. Thereafter, stirring was continued at room temperature for 3 hours, and thus obtained precipitate was filtered. The precipitate obtained was dried at 70° C. for 8 hours under vacuum. A mixture which was obtained by sufficiently mixing 50.0 g of the dried white solid and 6.5 g of water with sprayer was compression-molded with a tabletting machine (inside diameter: 3 cm) under a pressure of 1 ton/cm². The obtained tablets were pulverized, then molded catalyst of 1.0 to 2.0 mm was obtained using sieves. Solid less than 1.0 mm was recycled to conduct compression molding again. The obtained molded catalyst of 1.0 to 2.0 mm was dried at 70° C. for 8 hours under vacuum.

Next, 10.0 g of the molded body obtained as described above was packed in a glass column of an inside diameter of 16 mmϕ, a mixed liquid(1) of 150 ml of methanol with 3.0 g of concentrated hydrochloric acid(content: 36% by weight), a mixed liquid(2) of 100 ml of methanol with 1.0 g of concentrated hydrochloric acid, and, then 100 ml of methanol(3), in this order, were passed through the column under heating of 60° C. at LHSV of 6 h$^{-1}$. After removal of the liquid, the molded body was dried at 120° C. under vacuum of 10 mmHg for 1.5 hours.

4.0 Grams of the molded body obtained as described above was charged in a flask and mixed with 2.7 g of hexamethyldisilazane and 40.0 g of toluene, and the mixture was subjected to refluxing with heat under stirring for 1.5 hours. The liquid part was eliminated from the mixture by filtration, and the solid obtained was dried at 120° C. under vacuum of 10 mmHg for 2 hours to obtain a molded catalyst. The obtained molded catalyst had a specific surface area of 958 m²/g, average pore diameter of 30.9 Å and a pore volume of 0.74 cc/g.

Synthesis of Propylene Oxide(PO)

The molded catalyst obtained as described above was evaluated with a batch reaction apparatus (autoclave) using 25% of cumene hydroperoxide(CHPO) and propylene(C3'). 1.0 Gram of the catalyst, 30.0 g of CHPO and 16.6 g of C3' were charged in the autoclave to react them under autogenous pressure at a reaction temperature of 85° C. for a reaction time of 1.5 hours (containing temperature raising time). The reaction result is shown in Table 1.

Comparative Example 1

128.1 Grams of 16 wt % hexadecyltrimethyl ammonium hydroxide aqueous solution (containing 1.3% by weight of K ion) was stirred, 1.85 g of tetra-isopropyl orthotitanate and 10.0 g of 2-propanol were added dropwise thereto. After stirring of 30 minutes, 38.1 g of tetramethyl orthosilicate was added dropwise. Thereafter, the operation was carried out in the same manner as in Example 1. The obtained molded catalyst had a specific surface area of 714 m²/g, an average pore diameter of 33.6 Å and a pore volume of 0.60 cc/g.

Using the obtained molded catalyst, performance of the catalyst was evaluated with the batch reaction apparatus in the same manner as in Example 1. The reaction result is shown in Table 1.

TABLE 1

|  | Example 1 | Comparative Example 1 |
|---|---|---|
| Catalyst |  |  |
| K⁺ in mixture prepared |  |  |
| K⁺/Ti mol/mol | 0.5 | 6.7 |
| K⁺/template *1 mol/mol | 0.05 | 0.65 |
| Specific surface area m²/g | 958 | 714 |
| Average pore diameter Å | 30.9 | 33.6 |
| Specific pore volume cc/g | 0.74 | 0.60 |
| Reaction result |  |  |
| CHPO conversion % | 97.6 | 11.1 |
| PO/C3' selectivity % *2 | 98.4 | — |

*1: Hexadecyltrimethyl ammonium ion
*2: PO/C3' selectivity = produced PO mol/reacted C3' mol × 100

INDUSTRIAL APPLICABILITY

As described above, according to the present invention, there is provided a process for producing a titanium-containing silicone oxide catalyst which can be used for a reaction obtaining, for example, an oxirane compound from a hydroperoxide and an olefin type compound and which can exhibit high activity.

What is claimed is:

1. A process for producing a titanium-containing silicon oxide catalyst satisfying all of the following conditions (1) to (4):

(1): an average pore diameter of 10 Å or more, (2): a pore diameter of 90% or more of the total pore volume of 5 to 200 Å, (3): a specific pore volume of 0.2 cm³/g or more, and (4): a quaternary ammonium ion represented by the following general formula (I) is used as a template and then the template is removed $$[NR^1R^2R^3R^4]^+ \quad (I),$$

wherein, $R^1$ represents a linear or branched hydrocarbon group having 10 to 36 carbon atoms, and $R^2$ to $R^4$ represent an alkyl group having 1 to 6 carbon atoms which comprises the steps of:

obtaining a solid containing a catalyst component and a template by mixing and stirring a silica source, a titanium source and, as the template, the quaternary ammonium ion to prepare a solid, wherein an amount of an alkali metal in the mixture prepared is within a range of the following expression (II) or (III), $$\text{alkali metal/titanium} \leq 3 (\text{mol/mol}) \quad (II)$$

$$\text{alkali metal}/[NR^1R^2R^3R^4]^+ \leq 0.3 (\text{mol/mol}) \quad (III);$$

molding the solid;

removing the template from the molded solid by solvent extraction;

recycling the template contained in the extracted liquid and reusing it; and subjecting the molded solid after removing the template to silylation to obtain a silylated catalyst.

* * * * *